US00PP09453P

United States Patent [19]

Brown

[11] Patent Number: Plant 9,453

[45] Date of Patent: Feb. 13, 1996

[54] AGLAONEMA PLANT NAMED 'MANILA PRIDE'

[75] Inventor: B. Frank Brown, Valkaria, Fla.

[73] Assignee: Sunshine Foliage World, Zolfo Springs, Fla.

[21] Appl. No.: 384,526

[22] Filed: Feb. 1, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

A new and distinct cultivar of Aglaonema named Manila Pride characterized by its dark green leaves marked with silver-green and yellow, large upright growth habit, and pink petioles.

3 Drawing Sheets

The present invention comprises a new and distinct cultivar of Aglaonema, botanically known as *Aglaonema hybrida,* and referred to by the cultivar name Manila Pride.

The new cultivar is a product of a planned breeding program carried out by the inventor B. Frank Brown in Valkaria, Fla. The new cultivar is a product of a cross of presently unidentified parents of the following species parentage:

Seed parent: *Aglaonema panayensis;*

Pollen parent: *Aglaonema commutatum.*

Asexual propagation of the new cultivar by cuttings performed by the inventor in Valkaria, Fla. was used to increase the number of plants for evaluation and has demonstrated the stability of the combination of characteristics of the new cultivar from generation to generation.

The following observations, measurements and values describe plants grown in Zolfo Springs, Fla. under shadehouse conditions which closely approximate those generally used in horticultural practice.

The following traits have been repeatedly observed to be characteristics which in combination distinguish Manila Pride from other Aglaonema of the same general type, for example, the patented and well known cultivar Rembrandt, disclosed in U.S. Plant Pat. No. 7,440, and with which Manila Pride is compared.

1. The leaves of Manila Pride have more prominent silver markings, and fewer yellow-green markings than those of Rembrandt.

2. Plants of Manila Pride are larger, taller, and more upright than Rembrandt.

3. Plants of Manila Pride are best suited to larger pot sizes than Rembrandt.

4. Plants of Manila Pride have fewer branches than Rembrandt.

5. Plants of Manila Pride show little foliar damage when exposed to 40° F. for approximately 3 hours.

All color references are measured against The Royal Horticultural Society Colour Chart. Colors are approximate as color depends on horticultural practices such as light level and fertilization rate, among others, without, however any variances in genotype.

The drawings comprise color photographs and color photocopy.

The photo comprising Sheet 1 is a top perspective view of Manila Pride.

The photo on Sheet 2 is a top perspective view of comparison cultivar Rembrandt. The differences in foliage color between Manila Pride and Rembrandt will be apparent when sheets 1 and 2 are compared.

The color photocopy comprising Sheet 3 shows the detail of the color pattern on the upper and lower sides of typical, mature leaves of Manila Pride. The leaves are shown full size in the photocopy on Sheet 3.

The photograph comprising sheet 1 is of a plant of Manila Pride in a 26 cm pot approximately 24 months after planting a single four-leaf cutting and grown under appropriate growing conditions. The true colors of the leaves are more accurately depicted in Sheet 1 than the photocopy comprising Sheet 3. Colors are as accurate as possible with color illustrations of this type.

Origin: Seedling selected from a cross between an unknown cultivar of *Aglaonema panayensis* as the seed parent and an unknown cultivar of *Aglaonema commutatum* as the pollen parent.

Classification: *Aglaonema hybrida,* cv. Manila Pride.

Propagation: Asexual propagation either by division or tissue culture.

Plant: When a four-leaf cutting is grown in a 26 cm pot for 24 months under appropriate conditions, Manila Pride reaches a height of approximately 16 cm to 24 cm from the soil surface to the junction of the petioles of the last two (2) unrolled leaves, and a width of approximately 98 cm to 100 cm.

*Stem.*—Growth pattern: The stem is erect in growth and approximately 1.7 cm to 2.5 cm in diameter five (5) cm above the soil surface. Internode distance is approximately 0.9 cm to 1.5 cm three (3) cm above the soil. Color: Greener than but closest to 163D, mottled with 146A.

*Petiole.*—The following information is based on the fourth expanded leaf from the apex. Growth pattern: The petiole has fleshy edges extending from the midrib, referred to as wings. The wings are approximately 5 mm to 7 mm wide one-half (½) the distance from the petiole base to the wing apex. The wings extend from the base of the petiole to within approximately 4.6 cm to 7.1 cm of the base of the leaf. The apex of the wings is rounded. The petiole follows the stem axis but diverges from the axis approximately 15 cm to 19.5 cm from the leaf base, forming a horizontal distance from the edge of the stem to the leaf base of approximately 5.0 cm to 7.5 cm. Dimensions: The petiole is straight from its base to the tip of the wings, and often curved between the tip of the wings and the base of the leaf. The petiole is approximately 6 mm to 8 mm in diameter one-half (½) the distance between the top of the wing and the base of the leaf. The petiole is approximately 21 cm to 25.7 cm in length. Color: The petiole wings and the midrib are 27C, with blotches and streaks of 146A.

*Leaf.*—Growth pattern: The leaf is ovate with a cuspidate apex and a truncate to cordate base. The margin is entire. The leaf is asymmetric, with the side of the leaf unrolling first having less surface area than the side unrolling last. The leaf is oriented parallel to the stem axis at the time of full unrolling, changing to approximately 40 degrees from the stem axis as more leaves unroll above it. The midrib is straight. The leaf blade is flat or somewhat wavy from the midrib to the margin, and often wavy along the margin. Dimensions: For the pot size and growing time indicated, the largest leaves are approximately 30 cm to 32 cm long and approximately 10.5 cm to 13.2 cm wide. Average sized leaves are approximately 25 cm to 29 cm long and approximately 10.5 cm to 12.5 cm wide. The leaf is moderately thick. Midrib: The midrib is thick and prominent, recessed on the upper leaf surface and protruding from the lower surface. Primary veins: The primary veins are sunken into the upper surface and protrude slightly from the underside. The primary veins are the same color as the tissue surrounding them. The leaf blade is convex between the primary veins. Pattern: The upper leaf surfaces are dark green in base color, with large prominent silver-green chevrons following the primary veins and often coalescing to occupy much of the central leaf surface. The central area of the leaf is sparsely spotted with yellow-green. The midrib is spotted with yellow-green for approximately two-thirds (⅔) its length. The lower surface is medium green sparsely spotted with white in the central area of the leaf. The midrib is white with light green spots and streaks. Colors: Mature leaf: Upper surface, darker and greener than, but closest to 137A, with markings darker than, but closest to 191A. Yellow-green spots 145B-C. Midrib, 137A, with spots and streaks of 150C. Lower surface, darker and greener than, but closest to 147B with spots of 155A, 145D. Midrib, lighter than, but closest to 150D with spots of 145 A. Newly opened leaf: Upper surface, 137A-B with markings darker and more silver than, but closest to 148C. Yellow-green spots 145B-C. Midrib, 146B with spots and streaks of 150C-D. Lower surface, 146B with spots of 155A, 145D. Midrib, lighter than, but closest to 150D with spots of 145A. Axillary breaks: There are approximately 7 to 12 axillary breaks with at least one leaf expanded. Leaves will show true color and pattern by the first leaf. Inflorescence: Typical of Aglaonema and does not have commercial significance.

*Roots.*—Thick white roots with fine laterals.

General observation: Aglaonema Manila Pride is a large upright growing variety having dark green leaves prominently marked with silver-green chevrons and sparse yellow spots. The petioles are pink with spots of green. These combined characteristics make Manila Pride a unique new cultivar.

I claim:

1. A new and distinct cultivar of Aglaonema plant named Manila Pride, as illustrated and described.

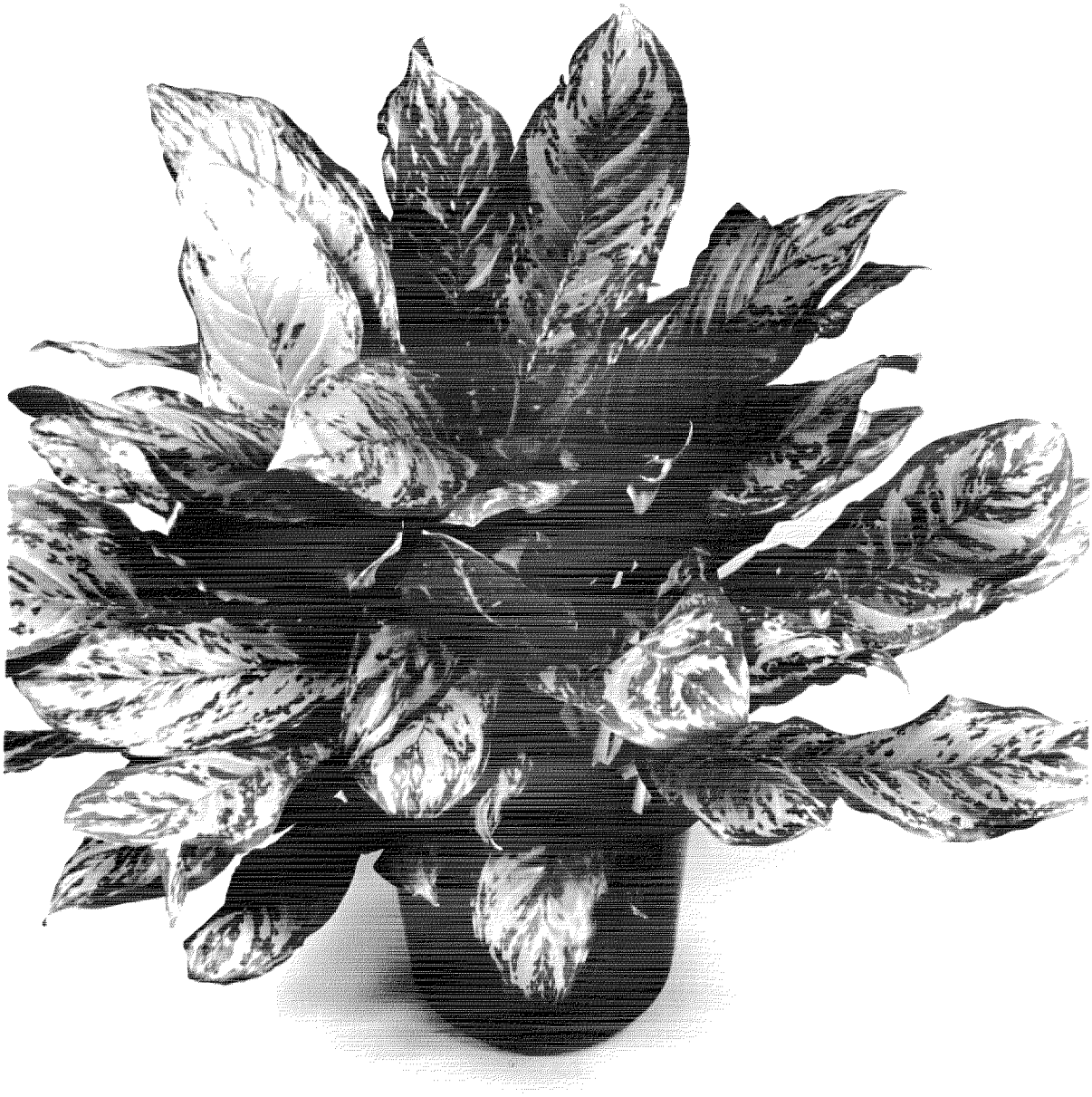

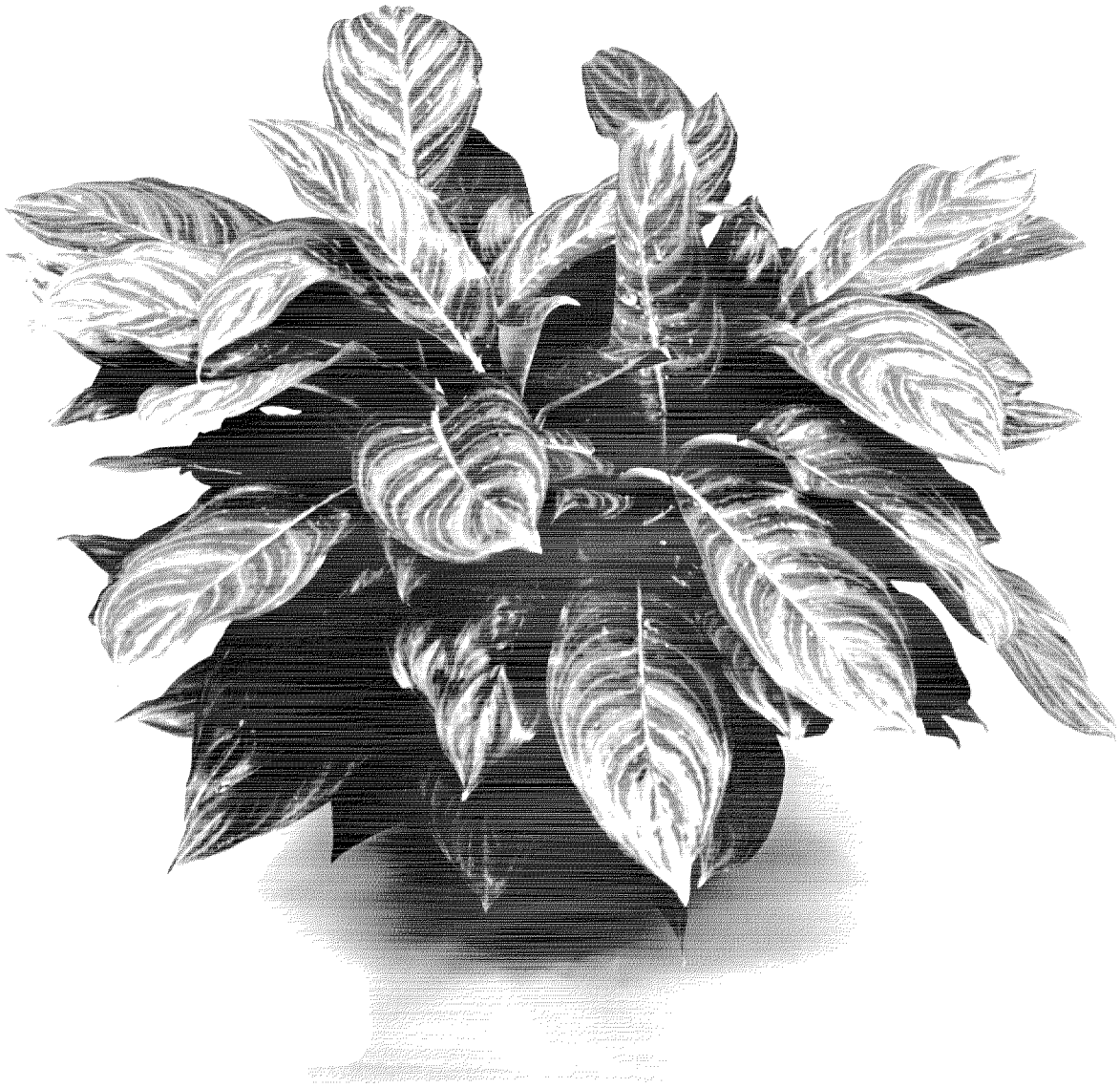

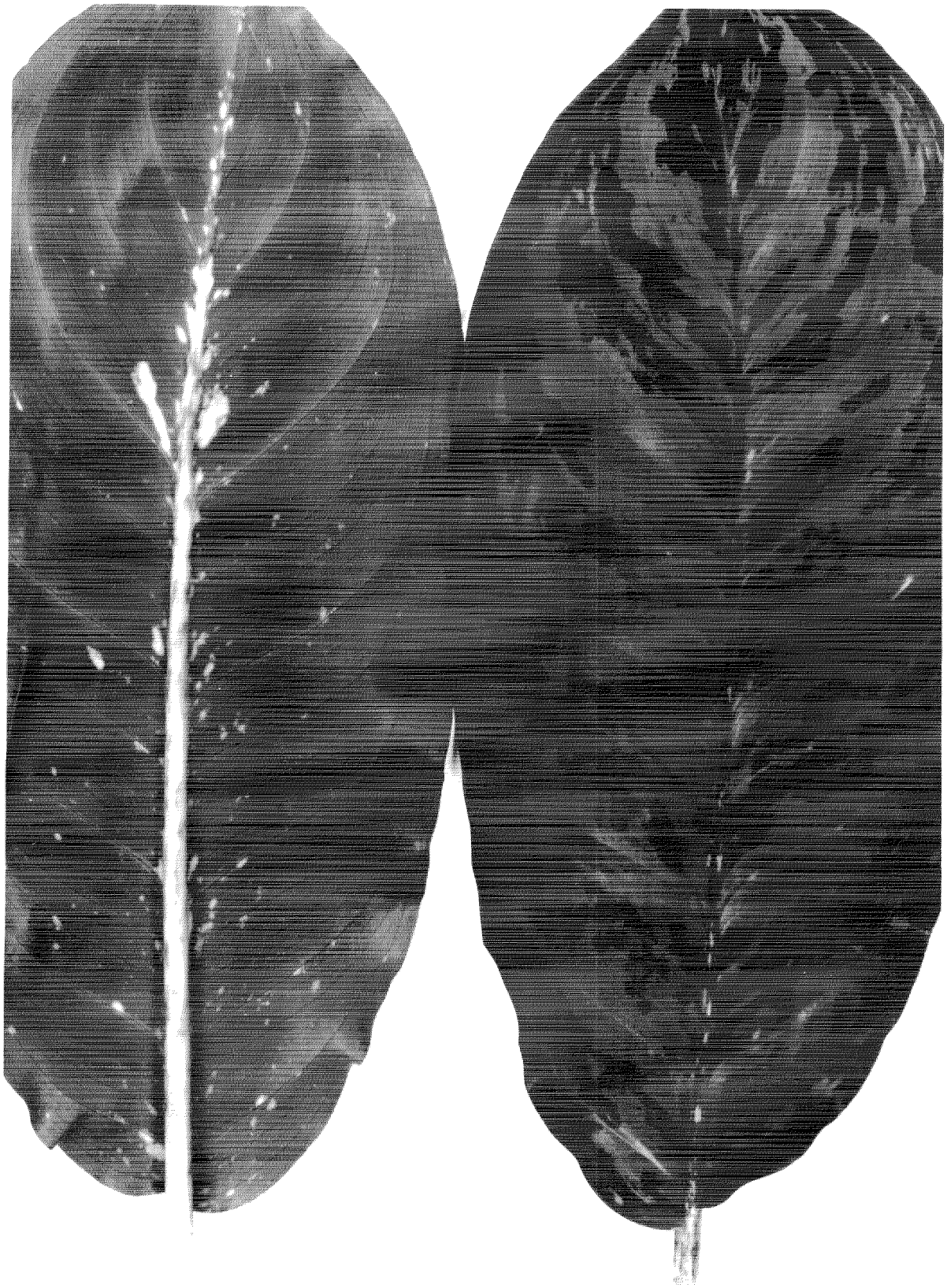

* * * * *